(12) United States Patent
Gotman (10) Patent No.: US 9,025,723 B2
(45) Date of Patent: May 5, 2015

(54) PRE-SCAN IMAGING WITH ROTATING GANTRY

(75) Inventor: Shlomo Gotman, Haifa (IL)

(73) Assignee: Koninklijke Philips N.V., Eindhoven (NL)

( * ) Notice: Subject to any disclaimer, the term of this patent is extended or adjusted under 35 U.S.C. 154(b) by 116 days.

(21) Appl. No.: 14/007,736

(22) PCT Filed: Mar. 30, 2012

(86) PCT No.: PCT/IB2012/051535
§ 371 (c)(1),
(2), (4) Date: Sep. 26, 2013

(87) PCT Pub. No.: WO2012/137112
PCT Pub. Date: Oct. 11, 2012

(65) Prior Publication Data
US 2014/0016740 A1   Jan. 16, 2014

Related U.S. Application Data

(60) Provisional application No. 61/471,255, filed on Apr. 4, 2011.

(51) Int. Cl.
*A61B 6/03* (2006.01)
*A61B 6/06* (2006.01)
*A61B 6/00* (2006.01)
*A61B 6/04* (2006.01)
*A61B 6/02* (2006.01)

(52) U.S. Cl.
CPC ............... *A61B 6/035* (2013.01); *A61B 6/032* (2013.01); *A61B 6/488* (2013.01); *A61B 6/5205* (2013.01); *A61B 6/0407* (2013.01); *A61B 6/54* (2013.01); *A61B 6/027* (2013.01)

(58) Field of Classification Search
CPC .......... A61B 6/03; A61B 6/032; A61B 6/035; A61B 6/44; A61B 6/4429; A61B 6/4435; A61B 6/4441; A61B 6/448; A61B 6/54
USPC .......................................... 378/4, 15, 20, 207
See application file for complete search history.

(56) References Cited

U.S. PATENT DOCUMENTS

| 4,573,179 | A | * | 2/1986 | Rutt | ................................. 378/10 |
| 5,379,333 | A | * | 1/1995 | Toth | ................................. 378/16 |
| 5,457,724 | A |   | 10/1995 | Toth | |

(Continued)

FOREIGN PATENT DOCUMENTS

| EP | 0825457 A2 | 2/1998 |
| WO | WO 2005000121 A1 * | 1/2005 |
| WO | 2005000121 A1 | 2/2005 |

*Primary Examiner* — Robert Kim
*Assistant Examiner* — David E Smith (57) ABSTRACT

A method includes identifying at least first and second angles of rotation of the rotating gantry at which first and second pre-scans are acquired, wherein the first and the angles of rotation are different angles, acquiring data, via the imaging system while rotating the rotating gantry, only during a pre-determined angular range about the first angle of rotation for a first plurality of rotations from the start to the end pre-scan positions and during the predetermined angular range about the second angle of rotation for a second plurality of rotations from the start to the end pre-scan positions, and reconstructing a first pre-scan based only on the data acquired during the predetermined angular range about the first angle of rotation and a second pre-scan based only on the data acquired during the predetermined angular range about the second angle of rotation.

20 Claims, 5 Drawing Sheets

(56) References Cited

U.S. PATENT DOCUMENTS

| | | |
|---|---|---|
| 2005/0041772 A1 | 2/2005 | Nishide |
| 2006/0182225 A1 | 8/2006 | Besson |
| 2007/0286332 A1 | 12/2007 | Gohno et al. |
| 2009/0034678 A1* | 2/2009 | Popescu .......................... 378/10 |
| 2009/0262885 A1* | 10/2009 | Bontus et al. ................... 378/11 |
| 2010/0177867 A1* | 7/2010 | Kozelj et al. .................... 378/20 |
| 2012/0243657 A1* | 9/2012 | O'Loughlin ..................... 378/16 |

* cited by examiner

PRE-SCAN IMAGING WITH ROTATING GANTRY

CROSS-REFERENCE TO PRIOR APPLICATIONS

This application is the U.S. National Phase application under 35 U.S.C. §371 of International Application No. PCT/IB2012/051535, filed on Mar. 30, 2012, which claims the benefit of U.S. Provisional Patent Application No. 61/471,255, filed on Apr. 4, 2011. These applications are hereby incorporated by reference herein in their entirety.

FIELD OF THE INVENTION

The following generally relates to acquiring one or more pre-scan images while rotating the rotating gantry of an imaging system, and is described with particular application to computed tomography (CT). Suitable CT based scanners include, but are not limited to, CT and CT hybrid scanners such as CT/PET (positron emission tomography), CT/SPECT (single photon emission tomography), CT/MR (magnetic resonance), and/or other scanners.

BACKGROUND OF THE INVENTION

A conventional computed tomography (CT) scanner includes a rotating gantry rotatably supported by a stationary gantry. The rotating gantry is configured to rotate about an examination region and carries an x-ray tube that rotates therewith. The x-ray tube is configured to emit radiation that traverses the examination region and a portion of an object or subject in the examination region. A subject support is used to position the object or subject at a static position for an axial scan or translate the object or subject through the examination region for a spiral/helical scan. A detector array is located across the examination region opposite the x-ray tube, detects radiation traversing the examination region and the object or subject, and generates projection data indicative thereof. A reconstructor reconstructs the projection data and generates volumetric of image data indicative thereof, which can be processed to generate one or more images.

Typically, before scanning the object or subject, one or more pre-scans (e.g., a scout/pilot image(s)) are performed, and the resulting data is used to facilitate creating an examination plan for the object or subject (e.g., determining the geometry of the scanned area), optimizing dose during scanning, correcting data (e.g., attenuation correction), facilitating post-processing the volumetric image data generated by a scan, etc.) For such a pre-scan, the rotating gantry and hence the x-ray tube is rotated to, if not already at, and held or maintained at a static angular position. Then, the subject support translates the object or subject through the examination region while the x-ray tube emits radiation and the detector detects radiation. The reconstructor reconstructs a two-dimensional (2D) image from the acquired data. Multiple such pre-scans have been performed for the same object or subject respectively with the x-ray tube at different angular positions.

The above-noted approach requires accelerating the rotating gantry (if the rotating gantry is not already moving) to move the x-ray tube to the pre-scan position, decelerating and stopping the rotating frame when the x-ray tube is at the requisite position, performing the pre-scan, and repeating the above steps one or more times for one or more additional pre-scans, and then accelerating the rotating frame for the scan. Unfortunately, decelerating the rotating frame for each pre-scan and accelerating the rotating frame after each pre-scan consumes time that could be spent with the patient, scanning one or more other patients, and/or otherwise used. Furthermore, when performing more than one pre-scan, the patient is moved through the examination region multiple times, one for each pre-scan, and irradiated with ionizing radiation multiple times, one for each pre-scan, and ionizing radiation may cause damage to the tissue in the irradiated region of the patient.

SUMMARY OF THE INVENTION

Aspects of the present application address the above-referenced matters and others.

According to one aspect, a method for performing at least two pre-scans while rotating a rotating gantry of an imaging system about an examination region during a same scan is illustrated. The method includes determining start and end pre-scan positions of a subject support carrying a subject to be imaged. The method further includes identifying at least a first angle of rotation of the rotating gantry at which a first pre-scan is acquired and a second angle of rotation of the rotating gantry at which a second pre-scan is acquired. The first and the angles of rotation are different angles, and the first and second angles are separated from each other by a non-zero angular range during which radiation does not traverses the examination region. The method further includes acquiring data, via the imaging system while rotating the rotating gantry, only during a predetermined angular range about the first angle of rotation for a first plurality of rotations from the start to the end pre-scan positions and during the predetermined angular range about the second angle of rotation for a second plurality of rotations from the start to the end pre-scan positions. The method further includes reconstructing a first pre-scan based only on the data acquired during the predetermined angular range about the first angle of rotation and a second pre-scan based only on the data acquired during the predetermined angular range about the second angle of rotation.

According to another aspect, an imaging system includes a stationary gantry and a rotating gantry rotatably supported by the stationary gantry and configured to rotate around an examination region. A subject support is configured to carry a subject and translate the subject through the examination region for scanning. The system further includes a radiation source carried by the rotating gantry and configured to emit radiation that traverses the examination region at least while the radiation source is rotating around the examination region. A radiation source controller controls the radiation source such that radiation traverses the examination region only during predetermined angular ranges about predetermined angles of rotation during each rotation of the rotating gantry. The predetermined angular ranges are separated from each other by one or more non-zero angular ranges during which radiation does not traverses the examination region. The system further includes a detector array configured to detect radiation traversing the examination region and generate a signal indicative of the detected radiation. A reconstructor reconstructs the signal to generate image data, wherein the reconstructor reconstructs a first pre-scan image based on data acquired during a predetermined angular range about a first predetermined angle for a first plurality of rotations of the rotating gantry and at least a second pre-scan based on data acquired during the predetermined angular range about a second predetermined angle for a second plurality of rotations of the rotating gantry.

According to another aspect, a method for acquiring at least two pre-scans corresponding to at least two different rotation angles with a computed tomography scanner while a rotating gantry supporting a radiation source of the scanner rotates about an examination region is illustrated. The method includes acquiring data at a first predetermined angle for a first set of rotations, and acquiring data at a second different predetermined angle for a second set of rotations. The method further includes combining the data acquired at the first predetermined angle for the first set of rotations to generate a first pre-scan, and combining the data acquired at the second predetermined angle for the second set of rotations to generate a second pre-scan.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
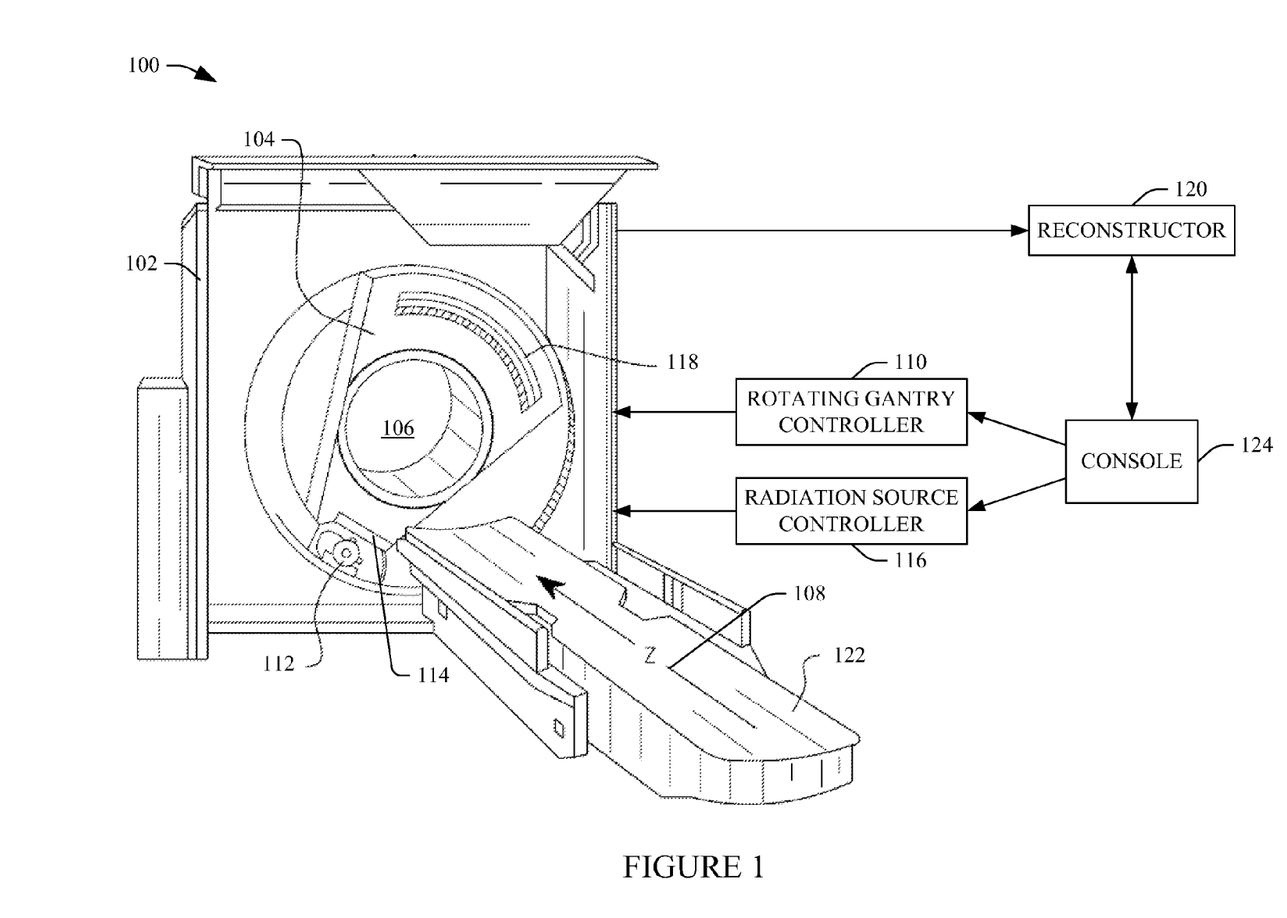
FIG. 1 schematically illustrates an example imaging system.

FIG. 1 illustrates an imaging system 100 such as a computed tomography (CT) scanner.

The imaging system 100 includes a stationary gantry 102 and a rotating gantry 104, which is rotatably supported by the stationary gantry 102. The rotating gantry 104 is configured to rotate around an examination region 106 about a longitudinal or z-axis 108.

A rotating gantry controller 110 controls rotational movement of the rotating gantry 104, including stopping and holding the rotating gantry 104 at a static position and rotating the rotating gantry 104 at one of one or more predetermined speeds for a pre-scan, a scan, and/or otherwise.

A radiation source 112, such as an x-ray tube, is supported by and rotates with the rotating gantry 104 around the examination region 106. The radiation source 112 can be activated to emit radiation that is collimated by a source collimator 114 to produce a generally fan, wedge, cone or otherwise shaped radiation beam that traverses the examination region 106.

A radiation source controller 116 controls the radiation source 112, including activating and deactivating (e.g., pulsing) emission of radiation that traverses the examination region 106. Generally, any known approach and/or other approach for activating and deactivating a radiation source to selectively emit radiation can be employed.

By way of non-limiting example, such can control may include applying and removing a source voltage (not shown) from the source 112 to turn the source 112 on and off, positioning a filter (not shown) in and out of the path of the radiation to substantially or fully attenuate radiation and allow radiation to enter and traverse the examination region 106, applying a grid voltage to a switching grid (not shown) to inhibit and allow electrons to flow from the cathode to the anode of the source 112, etc.

In another example, an annular ring of radiation attenuating material and material free regions or holes at desired angular positions (e.g., 90 degrees, 180 degrees, etc.) can be temporarily and stationarily affixed to the imaging system 100. In this instance, the source 112 emits radiation as it rotates about the examination region 106, however, the emitted radiation will only traverse the examination region 106 when the path of the radiation from the source 112 aligns with a hole in the ring.

A radiation sensitive detector array 118 detects radiation that traverses the examination region 106 and generates a signal indicative of the detected radiation. With a third generation imaging system (shown), the detector array 118 is supported by the rotating gantry 104, opposite the source 112 and across the examiner region 106. The detector array 118 may include a single or multiple rows of detector elements.

A reconstructor 120 reconstructs the signal and generates data indicative of the examination region 106. Such data may include one or more pre-scans (e.g., scout/pilot images) and/or or volumetric image data. For each pre-scan, the reconstruction may include combining data acquisitions obtained at a same rotational angular position but during different rotations of the rotating gantry 104.

A subject support 122, such as a couch, supports a subject such as a human or animal patient in the examination region 106 and is movable along the x, y and/or z-axis in coordination with the rotation of the rotating gantry 104 to facilitate pre-scan, and/or helical, axial, or other desired scanning trajectories.

A general purpose computing system serves as an operator console 124, and includes an output device such as a display and an input device such as a keyboard, mouse, and/or the like. The console 124 allows a user to operate the system 100 such as initiate a pre-scan, plan a scan, perform a planned scan, etc.

As described in greater detail below, in one instance, for a pre-scan, the console 124 controls the rotating gantry controller 110 to rotate the rotating gantry 104 about the examination region 106 while controlling the radiation source controller 116 to control the radiation source 112 such that radiation traverses the examination region 106 only during a predetermined angular range about one or more predetermined pre-scan angles and controlling the subject support 122 to translate the subject along the z-axis 108 through the examination region 106.

Such control allows for performing a pre-scan without having to move and decelerate and park the rotating gantry 104 at each pre-scan angle. Such control allows for performing a pre-scan without having to subsequently accelerate and rotate the rotating gantry 104 to another pre-scan angle or for a scan. As such, this approach may save time relative to a configuration in which the rotating gantry is parked at one or more pre-scan angles for one or more pre-scans and accelerated for a scan planned based on the one or more pre-scans. Moreover, the patient only has to be translated through the examination region 106 once for multiple pre-scan rather than once for each pre-scan, again, reducing pre-scan time.

Figure 2:
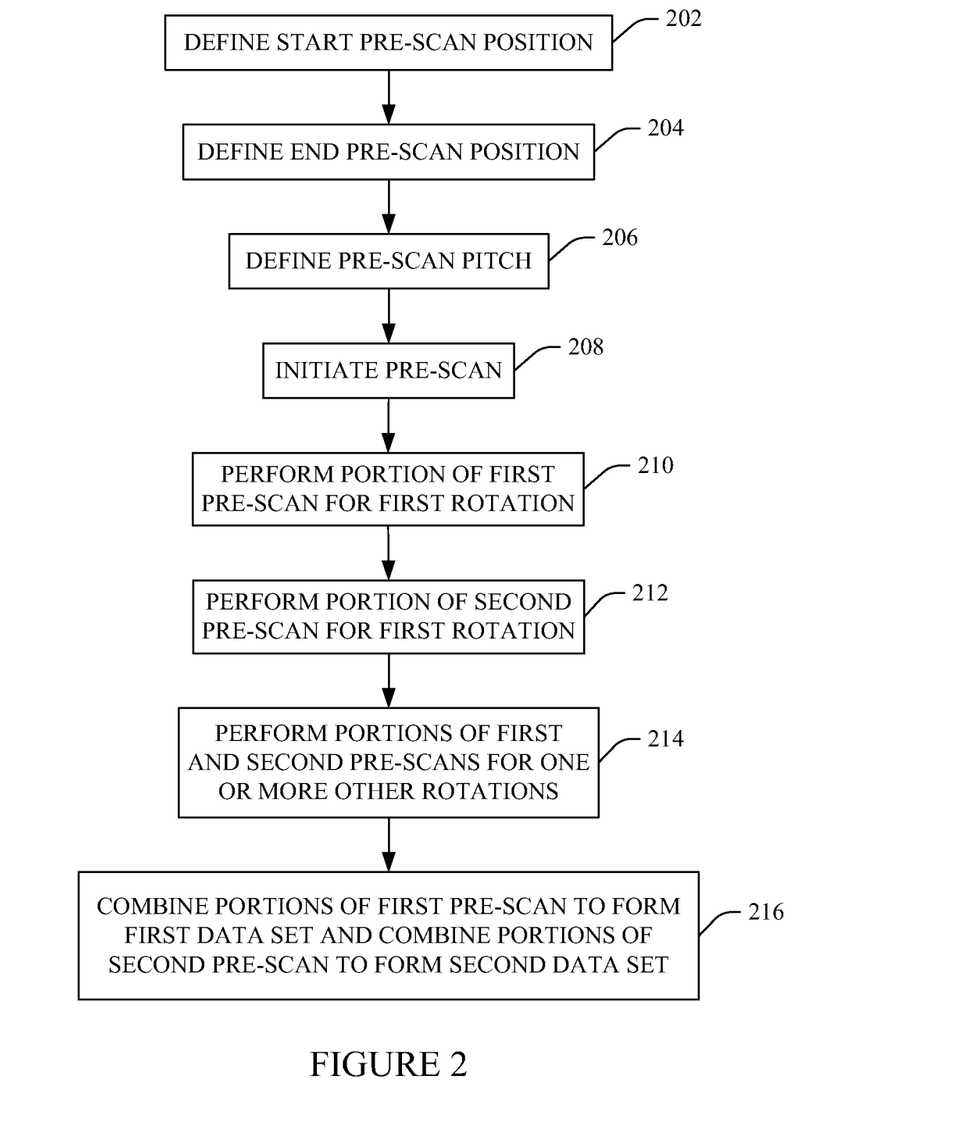
FIG. 2 illustrates a method for concurrently performing multiple pre-scans respectively at different angular ranges for each rotation a pre-scan while rotating the rotating gantry.
Figure 4:
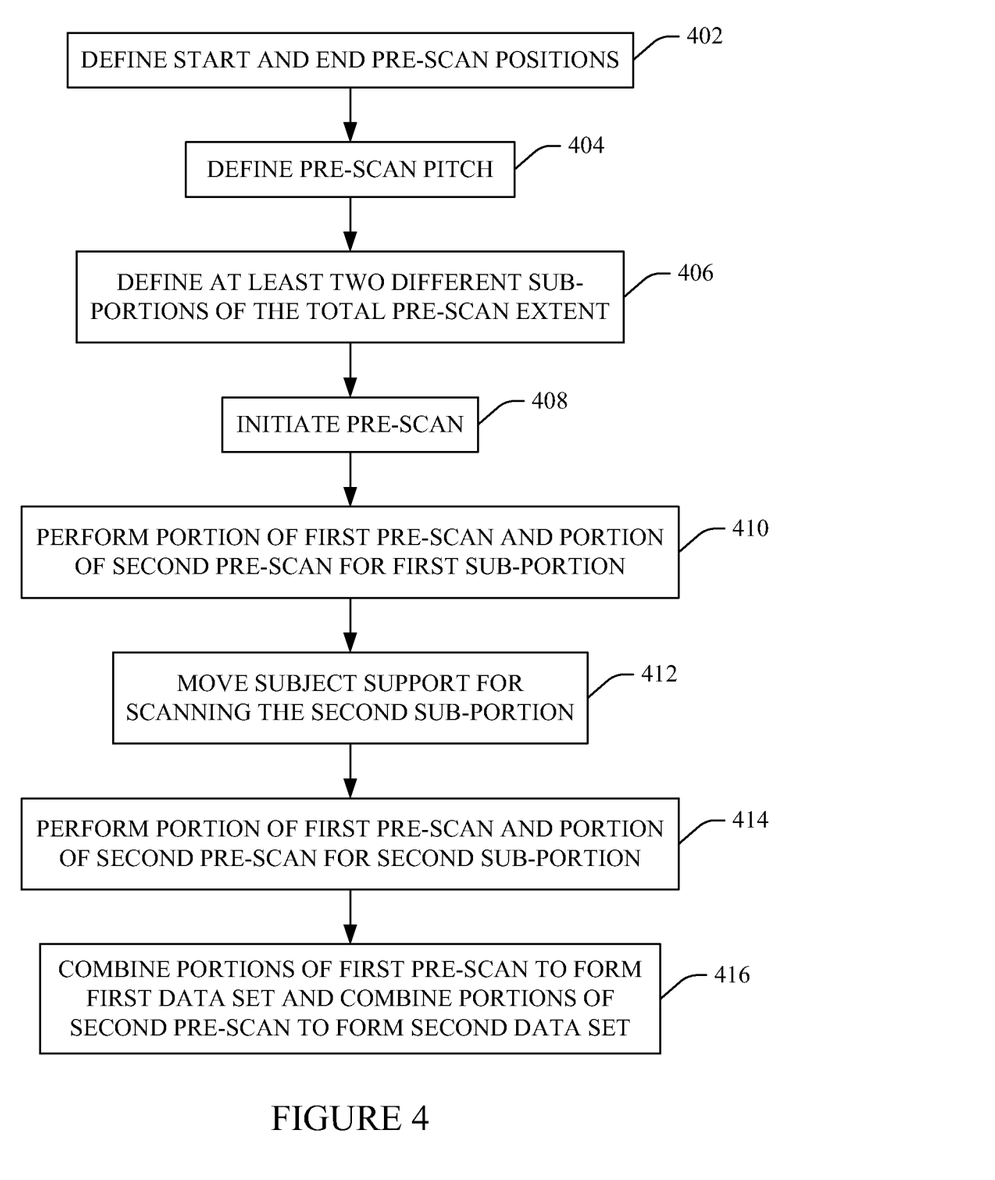
FIG. 4 illustrates a method for concurrently performing multiple pre-scans respectively at different angular ranges over a sub-set of the extent of the pre-scan while rotating the rotating gantry.
Figure 5:
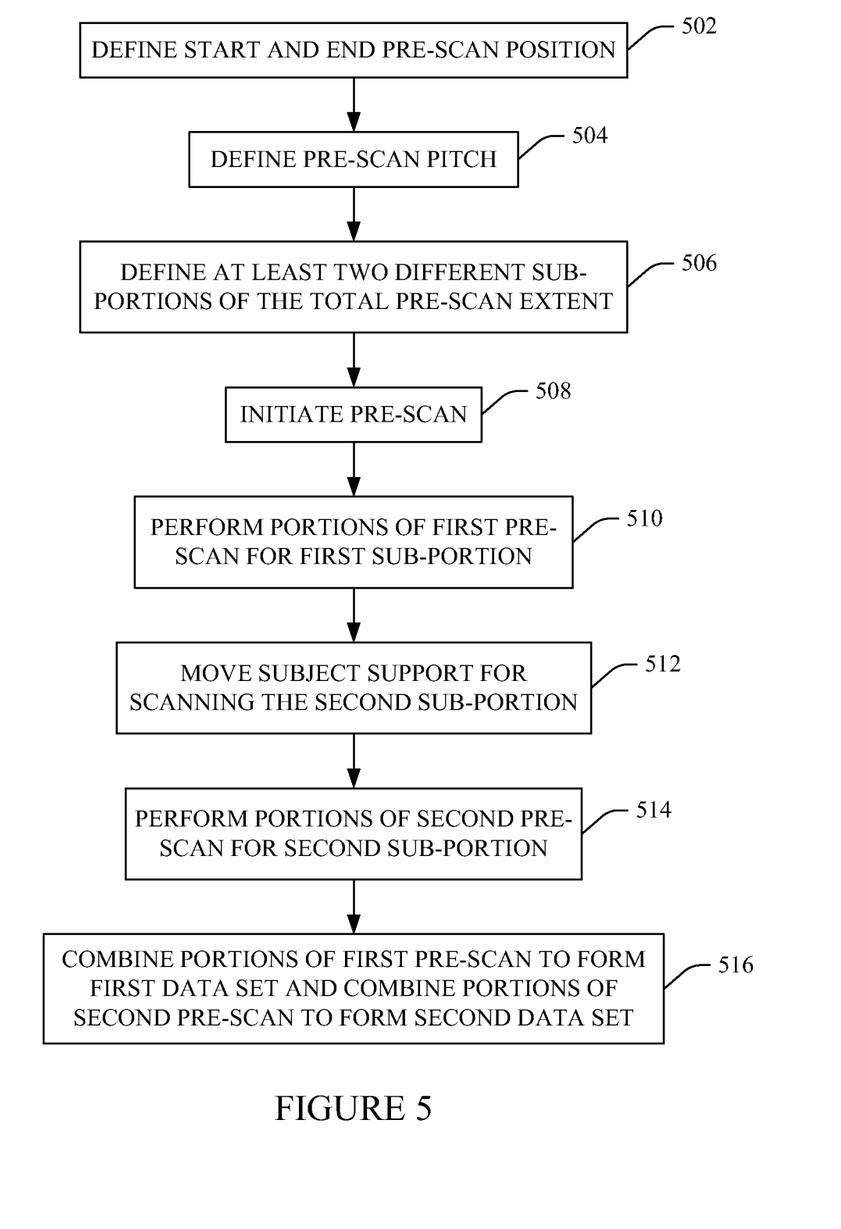
FIG. 5 illustrates a method for performing multiple pre-scans respectively at different angular ranges for different sub-sets of the extent of the pre-scan while rotating the rotating gantry.

FIGS. 2, 4 and 5 illustrate various non-limiting methods of performing multiple pre-scans with the imaging systems 100 of FIG. 1 while the rotating the rotating gantry 104.

It is to be appreciated that the ordering of the below acts is for explanatory purposes and not limiting. As such, other orderings are also contemplated herein. In addition, one or more of the acts may be omitted and/or one or more other acts may be included.

Initially referring to FIG. 2, a method for concurrently performing multiple pre-scans respectively at different angular ranges each rotation while rotating the rotating gantry 104 is illustrated.

At 202, a start pre-scan position is defined. For example, in one instance, the technician moves the subject support 122 (e.g., manually and/or via system controls) supporting a patient into the examination region 106 until a region of interest of tissue (e.g., the kidney) of the patient to be scanned is in or just outside of the examination region 106 on a side of the imaging system 100 in which the subject support 122 will advance into the examination region 106.

At 204, an end pre-scan position is defined. For example, in one instance, the technician enters a scan extent into the console 124 or controls located at the imaging system, for example, in connection with an outer shell of the stationary gantry 102.

At 206, a subject support 122 pitch of the pre-scan is defined. Suitable pitches include pitches of less then one, one and more than one. With a pitch of one, the subject support will translate a length of the z-axis detection coverage each rotation. As an example, with an eight (8) centimeter (cm) detector coverage in the z-axis direction, a pitch of one will result in the subject support moving eight (8) cm each rotation of the rotating gantry 104.

At 208, the pre-scan is initiated. For example, the clinician performing the procedure can invoke the console 124 via the mouse, keyboard, etc. to begin the pre-scan.

At 210, during a rotation of the rotating gantry 104 as the subject support 122 translates, the radiation source 112 rotates through a first predetermined acquisition arc path around a first rotation angle (e.g., 90 degrees) during which the source 112 emits radiation that traverses the examination region 106 and is detected by the detector array 118.

At 212, during the same rotation of the rotating gantry 104 as the subject support 122 translates, the radiation source 112 subsequently rotates through a second acquisition arc path about a second rotation angle (e.g., 180 degrees) during which the source 112 emits radiation that traverses the examination region 106 and is detected by the detector array 118.

Outside of the arc paths, the source 112 does not emit radiation that traverses the examination region 106 and is detected by the detector array 118.

The length of each arc path is a function of various parameters such as rotation speed, pitch, and/or other parameters. The following provides one non-limiting example for determining a suitable arc path length. With an acquisition time of around one millisecond (1 ms), a rotating gantry speed of half a second per rotation, and a pitch of one, the acquisition arc path would be 0.5 to 0.8 degrees such as 0.7 degrees for each of the first and the second acquisition arc paths. Other arc path lengths are also contemplated herein.

At 214, acts 210 and 212 are repeated one or more times for one or more other rotations until the patient support 122 has traveled to the end of the pre-scan or otherwise stopped.

At 216, the reconstructor 120 combines the acquisitions of the first acquisition arc path from each rotation to generate a first pre-scan and combines the acquisitions of the second acquisition arc path from each rotation to generate a second pre-scan. With a pitch of one, the acquisitions for an arc path are contiguous and can be sequentially or consecutively aligned to form a pre-scan.

With a pitch less than one, the acquisitions for an arc path would overlap. When combining such acquisitions, the overlapped portions may be averaged or otherwise combined. With a pitch greater than one, the acquisitions for an arc path will be separated by gaps. When combining such acquisitions, interpolation and/or other techniques can be used to derive data for the gaps.

A non-limiting example application is where it is desirable to have two or more pre-scans for one or more regions of tissue of interest.

Figure 3:
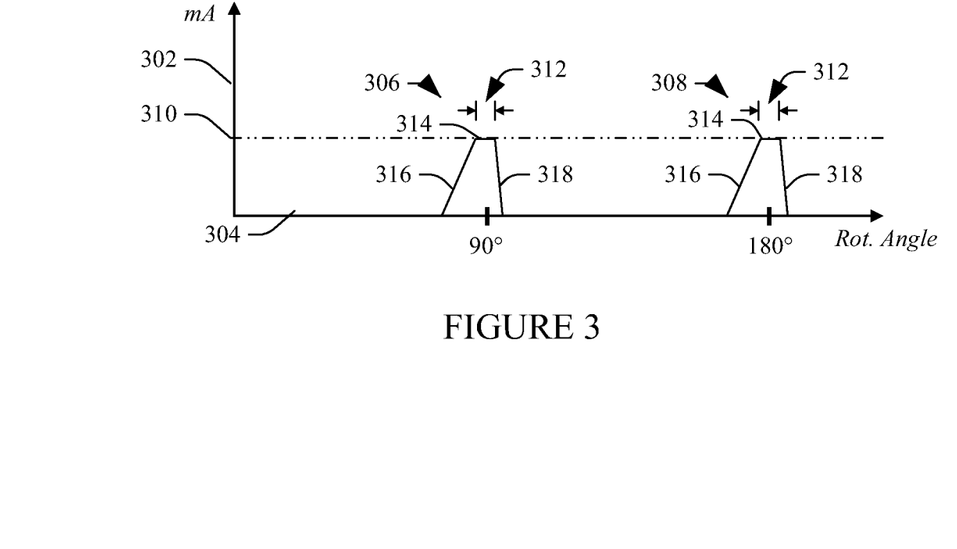
FIG. 3 shows an example timing diagram for two pre-scans acquired during the same rotation but at different angular ranges.

FIG. 3 shows an example timing diagram for the at least two pre-scans of FIG. 2, which are acquired during the same rotation but during different angular ranges. A first or y-axis 302 represents the tube current (e.g., milliampere, or mA) and a second or x-axis 304 represents the rotation angle. In this example, 0 degrees corresponds to a position of the rotating gantry 104 of FIG. 1 where the source 112 is located at the 3 o'clock position.

A first acquisition pulse 306 corresponds to the first angular range and is a range around 90 degrees in this example. A second acquisition pulse 308 corresponds to the second angular range and is a range around 180 degrees in this example. In other embodiments, the angles may be different, and the angular offset between the angles may be less than or greater than 90 degrees, for example, from 45 or less degrees to up to 180 degrees or more degrees.

Pulse peak 314 corresponds to a tube current tube 310. A pulse width 312 at the peak 314 of each pulse 306 and 308 corresponds to the acquisition arc path. In the example discussed above, the arc path is from 0.5 to 0.8 degrees such as 0.7 degrees. In other examples, the arc path may be less than 0.5 degrees and/or greater than 0.8 degrees.

A ramp up portion 316 and a ramp down portion 318 of each pulse 306 and 308 depend upon the speed at which the emitted radiation can be switched on and off. An area under each pulse 306 and 308 is such that each pre-scan deposits an amount of dose that corresponds to the dose deposited when performing a conventional pre-scan with the source 112 at a static position. The pulse widths and heights can be changed to change the deposited dose.

Turning to FIG. 4, a method for concurrently performing multiple pre-scans respectively at different angular ranges for a subset of the pre-scan extent while rotating the rotating gantry 104 is illustrated.

At 402, start and end scan positions are defined, for example, as described in connection with FIG. 2 and/or otherwise.

At 404, a subject support pitch of the pre-scan is defined, for example, as described in connection with FIG. 2 and/or otherwise.

At 406, at least two different sub-portions of the total pre-scan extent from the start position to the end position are identified. In this example, there is a gap between the two sub-portions, although in other examples the different sub-portions may partially overlap.

At 408, the pre-scan is initiated, for example, as described in connection with FIG. 2 and/or otherwise.

At 410, during rotations of the rotating gantry 104 as the subject support 122 translates through the first sub-portion, the radiation source 112 rotates through a first predetermined acquisition arc path each rotation during which the source 112 emits radiation that traverses the examination region 106 and is detected by the detector array 118, and the radiation source 112 rotates through a second different predetermined acquisition arc path each rotation during which the source 112 emits radiation that traverses the examination region 106 and is detected by the detector array 118. In this example, outside of the arc paths, the source 112 does not emit radiation that traverses the examination region 106 and is detected by the detector array 118.

At 412, once the subject support 122 translates through the first sub-portion, the subject support 122 translates to the second sub-portion without the source 112 emitting radiation that traverses the examination region 106 and is detected by the detector array 118.

At 414, during rotations of the rotating gantry 104 as the subject support 122 translates through the second sub-portion, the radiation source 112 rotates through the first predetermined acquisition arc path each rotation during which the source 112 emits radiation that traverses the examination region 106 and is detected by the detector array 118, and the radiation source 112 rotates through the second predetermined acquisition arc path each rotation during which the source 112 emits radiation that traverses the examination region 106 and is detected by the detector array 118. Likewise, outside of the arc paths, the source 112 does not emit radiation that traverses the examination region 106 and is detected by the detector array 118.

At 416, the reconstructor 120 combines the acquisitions of the first acquisition arc path from each rotation during the first and second sub-portions to generate a first pre-scan data set, and combines the acquisitions of the second acquisition arc path from each rotation during the first and second sub-portions to generate a second pre-scan data set. In instances in which more than two sub-portions are identified, the reconstructor 120 can likewise combine data there from to generate additional data sets.

A non-limiting example application is where there are two or more regions of interest of tissue to be scanned, and the two or more regions of interest are at least partially separated. By way of example, the extent of the scan may cover 40 cm, where the first sub-portion covers the first 5 cm and the second sub-portion covers the last 5 cm.

FIG. 5 illustrates a method for performing multiple pre-scans respectively over different angular ranges while the rotating gantry 104 during the same scan is illustrated.

At 502, start and end scan positions are defined, for example, as described in connection with FIG. 2 and/or otherwise.

At 504, a subject support pitch of the pre-scan is defined, for example, as described in connection with FIG. 2 and/or otherwise.

At 506, at least two different sub-portions of the total pre-scan extent from the start position to the end position are identified. In this example, there is a gap between the two sub-portions, although in other examples the different sub-portions may partially overlap.

At 508, the pre-scan is initiated, for example, as described in connection with FIG. 2 and/or otherwise.

At 510, during rotations of the rotating gantry 104 as the subject support 122 translates through the first sub-portion, the radiation source 112 rotates through a first predetermined acquisition arc path each rotation during which the source 112 emits radiation that traverses the examination region 106 and is detected by the detector array 118. Outside of the first arc path, the source 112 does not emit radiation that traverses the examination region 106 and is detected by the detector array 118.

At 512, once the subject support 122 translates through the first sub-portion, the subject support 122 translates to the second sub-portion without the source 112 emitting radiation that traverses the examination region 106 and is detected by the detector array 118.

At 514, during rotations of the rotating gantry 104 as the subject support 122 translates through the second sub-portion, the radiation source 112 rotates through a second predetermined acquisition arc path each rotation during which the source 112 emits radiation that traverses the examination region 106 and is detected by the detector array 118. The second arc path is different from the first arc path, and outside of the second arc path, the source 112 does not emit radiation that traverses the examination region 106 and is detected by the detector array 118.

At 516, the reconstructor 120 combines the acquisitions of the first acquisition arc path from each rotation during the first sub-portion to generate a first pre-scan data set and combines the acquisitions of the second acquisition arc path from each rotation during the second sub-portion to generate a second pre-scan data set. In instances in which more than two sub-portions are identified, the reconstructor 120 can likewise combines data there from to generate additional data sets.

A non-limiting example application is where there are two or more regions of interest to be scanned, and it is desired one of the at least two of the regions (e.g., the spine) from one angular position and another of the at least two of the regions (e.g., the whole body) from a different angular position.

It is to be appreciated that two or more of the above methods can be combined, in part or in full, with each other and/or other methods.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method for performing at least two pre-scans while rotating a rotating gantry (104) of an imaging system about an examination region during a same scan, comprising:
    determining a start and an end pre-scan positions of a subject support carrying a subject to be imaged;
    acquiring data, via the imaging system while rotating the rotating gantry, only during a predetermined angular range about a first angle of rotation for a first plurality of rotations from the start to the end pre-scan positions and during the predetermined angular range about a second angle of rotation for a second plurality of rotations from the start to the end pre-scan positions,
    wherein the first angle of rotation corresponds to a first material free region in an annular of radiation attenuating material at least one of temporarily and stationarily affixed to a rotating gantry and the second angle of rotation corresponds to a second material free region in the annular ring of radiation attenuating material, wherein a radiation source emits radiation as it rotates about the examination region, and the emitted radiation only traverse the examination region when a path of the radiation from a radiation source aligns with a material free region in the annular ring; and
    reconstructing a first pre-scan based only on the data acquired during the predetermined angular range about the first angle of rotation and a second pre-scan based only on the data acquired during the predetermined angular range about the second angle of rotation.

2. The method of claim 1, wherein the first and second plurality of rotations are the same rotations, thereby data is acquired during both the predetermined angular range about the first angle of rotation and the predetermined angular range about the second angle of rotation during each rotation.

3. The method of claim 1, wherein the first and second pluralities of rotations include all of the rotations from the start to the end pre-scan position.

4. The method of claim 1, wherein the first and second pluralities of rotations include only a sub-set of all of the rotations from the start to the end pre-scan position.

5. The method of claim 4, wherein the first plurality of rotations includes a first sub-set of all of the rotations and the second plurality of rotations includes a second different sub-set of all of the rotations.

6. The method of claim 5, wherein the first sub-set of all of the rotations is separated from the second sub-set of all of the rotations by at least one rotation.

7. The method of claim 5, wherein the second sub-set of all of the rotations includes at least one rotation in the first sub-set of all of the rotations and at least one rotation not in the first sub-set of all the rotations.

8. The method of claim 4, wherein first data corresponding to a first region of interest for first tissue of interest is acquired during the first plurality of rotations and second data corresponding to a second region of interest for second tissue of interest is acquired during the second plurality of rotations.

9. The method of claim 1, wherein the first pre-scan is reconstructed by sequentially aligning data acquisitions obtained during the predetermined angular range about the first angle of rotation for the first plurality of rotations to generate a first contiguous data set and the second pre-scan is reconstructed by sequentially aligning data acquisitions obtained during the predetermined angular range about the second angle of rotation for the first plurality of rotations to generate a second contiguous data set.

10. The method of claim 1, wherein a tube current of a radiation source (112) of the imaging system radiation is set to a level at which a dose deposited to the subject is about the same as the dose deposited to the subject when performing the pre-scans with the rotating gantry and hence the radiation source held at a static angular position when imaging the subject.

11. An imaging system, comprising:
a stationary gantry;
a rotating gantry rotatably supported by the stationary gantry and configured to rotate around an examination region;
a subject support configured to carry a subject and translate the subject through the examination region for scanning;
a radiation source carried by the rotating gantry and configured to emit radiation that traverses the examination region at least while the radiation source is rotating around the examination region;
an annular ring of radiation attenuating material and material free regions at two or more predetermined angular positions, at least one of temporarily and stationarily affixed to the rotating gantry, wherein the radiation source emits radiation as it rotates about the examination region, and the emitted radiation only traverse the examination region when a path of the radiation from the radiation source aligns with a free regions in the annular ring;
a detector array configured to detect radiation traversing the examination region and generate a signal indicative of the detected radiation; and
a reconstructor that reconstructs the signal to generate image data, wherein the reconstructor reconstructs a first pre-scan image based on data acquired with radiation traversing a first material free region for a first plurality of rotations of the rotating gantry and at least a second pre-scan based on data acquired with radiation traversing a first material free region for a second plurality of rotations of the rotating gantry.

12. The system of claim 11, wherein the first material free region and the second material free region are separated from each other by 45 degrees to 180 degrees.

13. The system of claim 11, wherein the radiation source emits radiation that traverses the examination region and is detected by the detector array at at least two different angles of rotation during at least one same rotation of the rotating gantry.

14. The system of claim 13, wherein the radiation source emits radiation that traverses the examination region and is detected by the detector array at at least two different angles of rotation during for all of the rotations in which data is acquired.

15. The system of claim 13, wherein the radiation source emits radiation that traverses the examination region and is detected by the detector array at at least two different angles of rotation during a first sub-set of all of the rotations in which data is acquired and a second different sub-set of all of the rotations.

16. The system of claim 15, wherein the first and second sub-sets of all of the rotations partially overlap.

17. The system of claim 15, wherein the first and second sub-sets of all of the rotations are separated by at least one rotation in which radiation is not detected by the detector array.

18. The system of claim 11, wherein the radiation source emits radiation that traverses the examination region and is detected by the detector array at a first angle during a first rotation of the rotating gantry and at a second different angle during a second different rotation of the rotating gantry.

19. The system of claim 11, wherein the reconstructor combines the data acquired at the first material free region to generate a first contiguous pre-scan data set and combines the data acquired during the second material free region to generate a second contiguous pre-scan data set.

20. A method for acquiring at least two pre-scans corresponding to at least two different rotation angles with a computed tomography scanner while a rotating gantry supporting a radiation source of the scanner rotates about an examination region, comprising:
acquiring data at a first predetermined angle for a first set of rotations, and acquiring data at a second different predetermined angle for a second set of rotations,
wherein the first predetermined angle corresponds to a first material free region in an annular ring of radiation attenuating material at least one of temporarily and stationarily affixed to the rotating gantry and the redetermined second angle corresponds to a second material free region in the annular ring of radiation attenuating material, wherein the radiation source emits radiation as it rotates about an examination region, and the emitted radiation only traverse the examination region when a path of the radiation from a radiation source aligns with the first and second material free regions in the annular ring; and
combining the data acquired at the first predetermined angle for the first set of rotations to generate a first pre-scan, and combining the data acquired at the second predetermined angle for the second set of rotations to generate a second pre-scan.

* * * * *